United States Patent
Van Romunde et al.

(10) Patent No.: US 7,490,051 B1
(45) Date of Patent: Feb. 10, 2009

(54) SYSTEM AND METHOD FOR STEERING INTERRELATED ACTIONS

(76) Inventors: Leo K. Van Romunde, Stekelbrem 33, 3068 TB Rotterdam (NL); Claude Paul Kaiser, Benoordenhoutseweg 243, 2596 GB Den Haag (NL)

( * ) Notice: Subject to any disclaimer, the term of this patent is extended or adjusted under 35 U.S.C. 154(b) by 0 days.

(21) Appl. No.: 09/402,563

(22) PCT Filed: May 28, 1998

(86) PCT No.: PCT/EP98/03195

§ 371 (c)(1),
(2), (4) Date: Oct. 5, 1999

(87) PCT Pub. No.: WO99/41686

PCT Pub. Date: Aug. 19, 1999

(30) Foreign Application Priority Data

Feb. 11, 1998 (BE) .................................. 9800103

(51) Int. Cl.
*G06F 9/44* (2006.01)
(52) U.S. Cl. .............................................. 705/7; 705/1
(58) Field of Classification Search .................. 705/1, 705/7, 8, 9, 10; 395/202
See application file for complete search history.

(56) References Cited

U.S. PATENT DOCUMENTS 5,060,980 A * 10/1991 Johnson et al.
5,583,758 A * 12/1996 McIlroy et al. ................. 705/2
5,781,904 A * 7/1998 Oren et al. .................... 707/100
6,021,202 A * 2/2000 Anderson et al. ............. 380/25

FOREIGN PATENT DOCUMENTS

WO    WO 99141686    *    8/1999

OTHER PUBLICATIONS

"Merriam -Webster's Collegiate Dictionary Tenth Edition", copyright 1997.*
"Practice guidelines and healthcare telematics: towards an alliance", C. Gordon, Health Telematics for Clinical Guidelines and Protocols, 1995.*

* cited by examiner

*Primary Examiner*—John W Hayes
*Assistant Examiner*—Rob Wu
(74) *Attorney, Agent, or Firm*—Lahive & Cockfield, LLP; Kevin J. Canning

(57) ABSTRACT

The invention relates to a method for electronically storing, retrieving and/or modifying records and for sequentially steering a process of interrelated actions in respect of said records, using a computer system that includes a display unit, an input unit, a memory unit and a processing unit. The method employs at least one recorded catalogue of recommended actions. The recorded catalogue(s) of recommended actions comprise hierarchised sequences of alternative actions. The method generates electronic forms which include a list of recommended actions, information-input requests and/or decision-requests, in function of the hierarchised sequences of alternative actions of the catalogue of recommended actions, and in function of the past history of actions. The invention also relates to a computer system programmed to operate such a system.

21 Claims, 1 Drawing Sheet

Annotated Sheet Showing Changes

Annotated Sheet Showing Changes

SYSTEM AND METHOD FOR STEERING INTERRELATED ACTIONS

Figure 1:
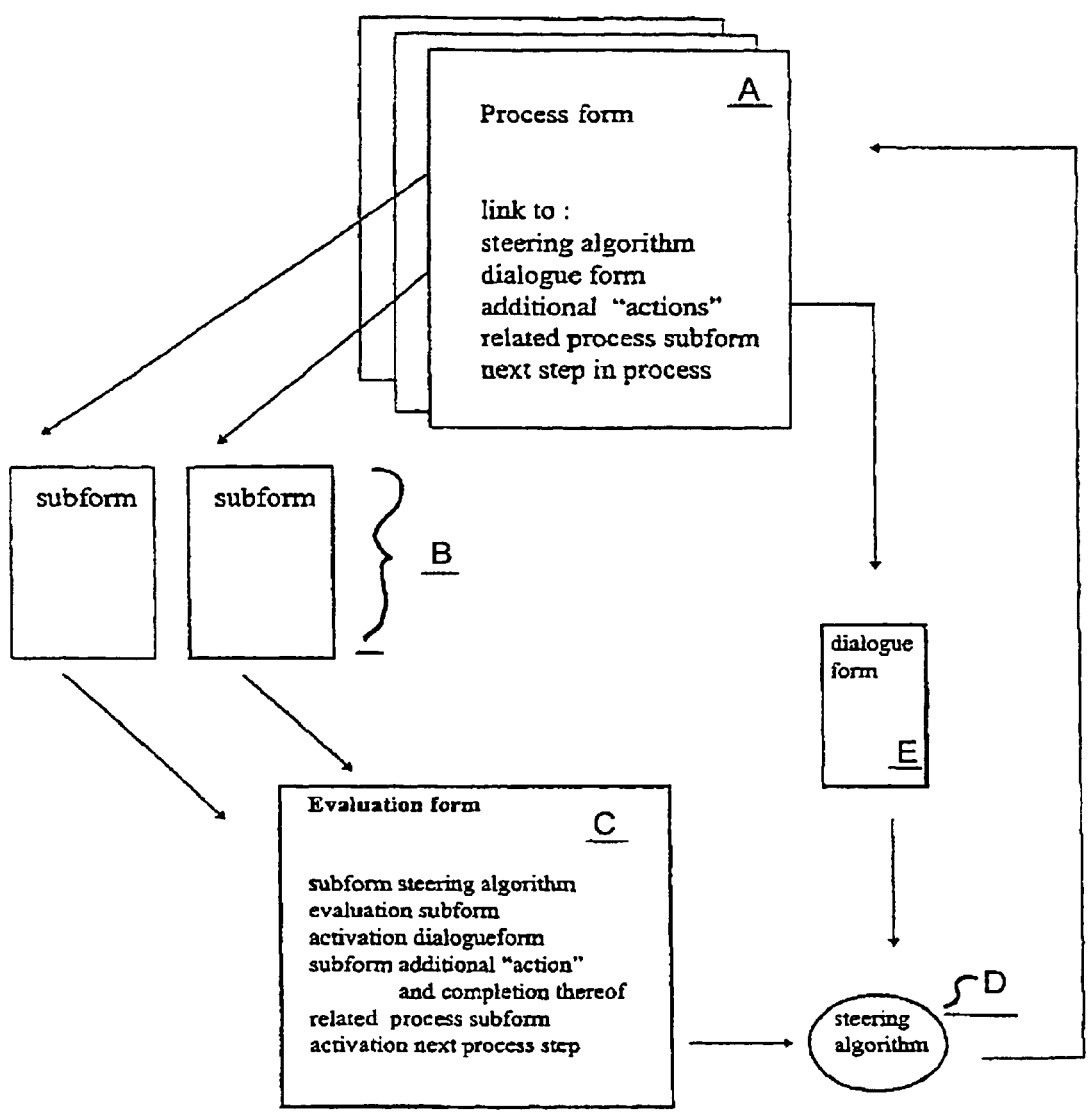

The invention relates to a method for electronically storing, retrieving and/or modifying records and for sequentially steering interrelated actions in respect of said records, using a computer system.

Methods for electronically storing, retrieving and/or modifying records for office management are generally known.

Reference is made for instance to the "LOTUS NOTES" software and "LOTUS DOMINO NOTES" software distributed by Lotus Development Corporation.

Such methods are often also adapted, or can be adapted in known ways, to be able to manage sequential actions in an overall procedure.

The known office management systems referred to above are, by design, easily adaptable for handling various standardised procedures (so called "applications" of the basic software), for instance by incorporating a catalogue of actions into the management system, but these known systems are not adapted for the needs of individual users who use a procedure record as a mere guideline for establishing working procedures suitable to variable individual situations.

The problem underlying the present invention is to satisfy the needs of the latter type of users of office management systems and to provide them a technical tool for the interactive implementation of interrelated action sequences.

Applicants of this patent have found a solution to this problem in the new method according to their invention, for electronically storing, retrieving and/or modifying records and for sequentially steering a process of interrelated actions in respect of said records, using a computer system comprising a display unit, an input unit, a memory unit and a processing unit, and involving at least one recorded catalogue of recommended actions, in which method the recorded catalogue(s) of recommended actions comprises/comprise hierarchised sequences of alternative actions, and which method generates electronic forms comprising a list of recommended actions, information-input requests and/or decision-requests (so-called dialogue-forms/subforms), in function of the hierarchised sequences of alternative actions of the catalogue of recommended actions, and in function of the past history of actions.

In this way the recorded catalogue of recommended actions operates as a unavoidable but adaptable and flexible guideline for the user in the process he is following.

In a preferred embodiment of the invention, the recorded catalogue(s) of recommended actions comprises/comprise electronic selection algorithms in respect of the hierarchised sequences of alternative actions.

According to a further feature of this embodiment of the invention the selection algorithms in respect of the hierarchised sequences of alternative actions are integrated in the electronic forms which are generated by the method.

In another preferred embodiment of the invention, which may be combined with other preferred embodiments of the invention, the method is appropriately applied as a procedure of interrelated actions involving a number of sequential procedure steps, wherein for each subsequent step in the procedure the method generates at least one process-form (which may be hidden, hideable and/or visualisable) and one visible evaluation form.

According to a further feature of this embodiment of the invention the evaluation form also comprises information from the records of the system relevant for any decision-request involved in said evaluation form.

According to the invention the method may furthermore very suitably involve that a record of all information used/entered when operating the method (i.e. all information contained/involved in all forms, actions, decisions, etc. used in applying the method) is stored in the memory unit of the system, for instance for the purpose of measurements of the effectivity and/or efficiency of effects and/or results of the procedure.

The expression "record" as used here refers to a capability of the method to store information in a retrievable way in the system.

In the method according to the invention the recorded catalogue(s) of recommended actions may very easily be updated, which in itself constitutes a distinctive feature of the invention.

In still another embodiment of the invention, which may also be combined with other preferred embodiments of the invention, the method may very appropriately involve a supervising organization for the purpose of quality control and quality improvement of the method.

Thus the supervising organization may very appropriately evaluate the effectivity and/or efficiency of effects and/or results based on the records of information (forms, actions and decisions) used/entered, stored during use by several users of the method, in accordance with one of the preferred embodiments of the invention, and up-date the recorded catalogue(s) of recommended actions in function of said evaluation.

The invention also provides a computer system for electronically storing, retrieving and/or modifying records and for sequentially steering interrelated actions in respect of said records, comprising a display unit, an input unit, a memory unit and a processing unit, in which said memory unit of the computer system comprises a recorded catalogue of actions with a recommended procedure sequence of the actions, in which said memory unit of the computer system comprises at least one recorded catalogue of recommended actions involving hierarchised sequences of alternative actions, and said processing unit of the computer system is programmed to generate electronic forms comprising a list of recommended actions, information-input requests and/or decision-requests, in function of the hierarchised sequences of alternative actions of the catalogue of recommended actions, and in function of the past history of actions.

In the computer system according to the invention the recorded catalogue(s) of recommended actions in the memory unit may very suitably comprise electronic selection algorithms in respect of the hierarchised sequences of alternative actions.

Preferably the processing unit of the computer system is programmed to integrate the selection algorithms in respect of the hierarchised sequences of alternative actions into the electronic forms.

According to a further feature of the computer system, its processing unit is preferrably programmed to generate one hidden or hideable process-form and one visible evaluation form for each step in the procedure of interrelated actions steered by computer system.

The processing unit of the computer system may also very suitably be programmed to integrate into the evaluation form any information from the records which is relevant for any decision-request involved in said evaluation form, and/or to store a record of the information (forms, actions and decisions) used/entered during the process, into the memory unit of the computer system.

The method according to the invention can very suitably serve as a tool for assisting a professional in implementing instructions in an interactive way. More in particular the method can (assist a professional to) implement a series of actions and/or tasks which have to be performed in a defined order, i.e. sequentially, in order to achieve a defined objective.

The method may for instance very suitably provide technical assistance for the (sequential) implementation of series of medical acts sometimes referred to as medical guidelines.

A fundamental feature of the method according to the invention lies in the fact that an hierarchy is assigned to the various steps or forms involved in the method.

Another fundamental feature lies in the fact that the recommended procedure sequence is integrated in the steps or forms used in the method.

According to the method a relation is established between the various types of forms, which relation has a certain order.

The hierarchy makes it possible to transfer a group of forms, such as the forms pertaining to one specific client, in one operation into one file ("Lotus" uses the expression folder). This is achieved by the concept of main files and related files (files with assignments). When transferring a main form all related forms are transferred at the same time.

The users of the method can thus constitute files with any desired content and archive those in any desired way.

A main form can comprise one or more sub-forms. A subform comprises a portion of the form. A subform can be integrated in several forms.

This feature of the known office management systems is mainly used in administrative applications for those parts of the forms which are the same, for instance for letter-heads, addresses, personal data, etc.

In the method according to this invention this feature is applied to allow operating in sequential steps according to a so-called protocol-procedure or guideline-procedure, i.e. according to recommended procedure-sequences.

Guideline-procedures are nowadays considered as an ideal means for managing and controlling both quality and costs. This is particularly the case in medical and welfare activities.

In practice there are however no appropriate means to monitor or control the actual use nor the correctness of guidelines and/or guideline procedures.

In the medical and welfare field it is thus for instance not known whether individual practitioners do indeed, in practice, have the guidelines at their disposal, nor whether they actually use these and with what result.

The quality of recommended procedures depends on the competence and knowledge of those who are responsible for drafting these procedures. Competence and knowledge are, by definition, limited. Recommended procedures or guidelines are therefore no more than the condensation of the knowledge of certain experts at a certain moment.

This also involves that for optimal use recommended procedures should always allow proper individual initiative.

The method according to the invention allows the user to
  always take notice of the appropriate procedure or procedure step/guideline step, regardless of the overall number of procedures/procedure steps/guideline steps;
  apply or not apply a procedure/procedure step/guideline step;
  judge the eventual effect.

The method does therefore not involve a compulsory decision tree.

The method is a tool to assist the skilled professional in the optimal decision making based on the knowledge and information available at the moment of decision.

The method provides a means for acting in a conscious and testable way.

The technical concepts of the invention, as defined hereabove, can be embodied by application of known office management software, and in particular by means of "LOTUS NOTES" or "LOTUS DOMINO NOTES" software, distributed by Lotus Development Corporation, which constitutes a preferred embodiment of the invention.

The following table illustrates the capabilities offered by the LOTUS NOTES software and the features of the invention specifically requiring these capabilities

| Feature required by the invention | Capability of LOTUS NOTES/ LOTUS DOMINO NOTES |
|---|---|
| hierarchy of forms | LOTUS NOTES folders |
| variable content of the process- or guideline-forms for each step in the procedure-sequence (guideline-step forms) | LOTUS NOTES subforms |
| steering via guidelines and guideline steps (for example medical guideline-form and medical evaluation form) | multiple forms having identical sub-forms |
| exchangeability of guideline steps | replication capability of LOTUS NOTES |
| exchangeability of process-results (for example results of medical treatments) | replication capability of LOTUS NOTES |

The method according to the invention comprises the following original concepts

| Process-forms (Guideline-step forms) involve following features | Evaluation forms involve following features |
|---|---|
| links | subforms |
| subforms | links to dialogue-(sub)forms |
| next guideline step in default situation | |
| requests for additional tests necessary in current guideline step in default situation | the ability to copy information from guideline step forms |

According to a specific embodiment of the method of this invention, these original concepts may be implemented by incorporating the following features in the process forms and evaluation forms, as better understood by reference to FIG. 1 and to the table below, wherein the reference numerals in the table correspond to the reference numerals shown in FIG. 1. FIG. 1 schematically represents the links between process forms (guideline-step forms) and evaluation forms via subforms, as well as the links with dialogue forms and with steering algorithms.

| Process form (guideline-step form) (A) | Evaluation form |
|---|---|
| link to steering (selection) algorithm | steering algorithm subform (D) |
| link to evaluation-subform (B) and evaluation-subform (B) itself | evaluation-subform (B) |
| link to dialogue-form (E) | possibility to activate dialogue-form (E) |
| link to additional tests, subform additional tests and | subform additional tests and completion of additional tests |

-continued

| Process form (guideline-step form) (A) | Evaluation form |
|---|---|
| standard completion of additional tests | |
| (optional) link to related procedures (such as clinical trial subforms) and the corresponding guideline-step forms | (optional) related procedures subforms |
| link to next guideline step in accordance with guideline (steered by algorithm) (D) | possibility to activate next procedure step in accordance with guideline (steered by algorithm) (D) |

The main features of the method according to the invention as set forth in the above table are shown in FIG. 1 which schematically illustrates the links between process forms (guideline-step forms) (A) and evaluation forms (C) via subforms (B), and the links with dialogue form (E) and with steering algorithms (D).

To implement these links the structure for composing the evaluation form is preferably contained in the guideline-step forms.

More specifically, the guideline-step forms contain indications about which subforms and dialogue forms are to be used for the evaluation form to be generated from said guideline-step form. This happens most suitably by specifying a name ("short designation") assigned to these subforms and dialogue forms.

The following table illustrates what and how this can be done for in particular the guideline-step form and the evaluation form:

| | Guideline-step form | Evaluation form |
|---|---|---|
| Name of the guideline step | Name is specified | Name is computed by algorithm subform |
| Questionaire- or clinical subform (consultation form) | Name is specified. Subform is then visualised. | Name is retrieved from corresponding guideline-step form. Subform is then visualised. |
| Request-form for additional tests | Name is specified. Subform is then visualised. Then default settings are specified. | Name is retrieved from corresponding guideline-step form. Subform is then visualised. Then all initial data are retrieved from corresponding guideline-step form. |
| Steering algorithm subform | Name is specified | Name is retrieved from corresponding guideline-step form. Subform is then incorporated in evaluation subform. It contains one or more fields which are automatically calculated and which establish the next step based on the available information |
| Dialogue form | Name is specified | Name is retrieved from corresponding guideline-step form. It can be activated by evaluation form. Purpose is to recall additional information required to establish |
| Link to next step by default | Name is specified | next step. Name is retrieved from corresponding guideline-step form. Name can be used in algorithm to establish next step |
| Clinical trial subform (optional) | Name is specified Subform is then visualised. | Name is retrieved from corresponding guideline-step form. Subform is then visualised. |

The preferred embodiment of the invention thus allows the creation of a file with unique properties (for instance a medical file)
  integration of guideline steps in evaluation forms;
    modifying a guideline-form automatically involves modification of the evaluation form;
  easy management of large numbers of guidelines by (expert) supervisor(s), such as a supervising "organization" or authority, for instance a profession-group or association;
  easy distribution of guidelines;
  freedom to deviate from guidelines or guideline steps;
  insight (monitoring) concerning activities and qualitative/quantitative effects The operation, in practice, of preferred embodiments of the method according to the invention, in particular in the medical area, is illustrated by the following example:

In order to operate the method, a coordinating body/centre/authority is required to establish the guidelines. This coordinating centre can for instance be a scientific association or a so called "integral cancer centre", but can also be an individual practitioner, such as a doctor, or partnership of professionals. In addition a managing and/or supervising organization is required, responsible for distributing the guidelines for/into the method.

In practice there will be an exchange of guidelines and/or guidelines between the coordination and supervising centres, and the "workstations", i.e. the participating professionals.

This means also that the knowledge corresponding to a (super) expert becomes available to all users of the method, in the form of measurable guidelines.

In the case of medical applications, the method according to the invention comprises (in analogy with conventional medical "files"):

1—registration-forms, in which all relevant data of the patient can be mentioned;
2—consultation-forms: i.e. guideline-steered forms (see item 5), in which the examination results are indicated;
3—request-forms for additional examination/tests;
4—result-forms;
5—dialogue screens (forms), on which the doctor can indicate his judgement (the resulting sum of his conclusions of the examination, the results of the additional examinations/tests and his knowledge), and on the basis of which, inter alia, the next guideline-step or procedure-step is selected;
6—guideline-forms: these forms define, for each consultation, the content of the consultation-forms: each time it will look different from a previous or next one; furthermore the guideline-forms stipulate which test-requests (laboratory-requests, requests for X-ray photographies, etc.) should be made in accordance with the standard guideline step, and, if applicable, when a next visit should take place. In fact the guideline or procedure will consist of a series of guideline-forms.

In practice things will proceed as follows:
1—A patient comes to a consultation.
2—The doctor or a secretary establishes a new "file" by filling in the registration form.
3—By means of a dialogue-screen (form), in which a number of questions are asked, a first guideline-form is selected.
4—The patient visits the doctors consultation.
5—The content of the consultation-form is established based on the selected guideline-form. The requests for additional tests (for instance bloed- and urine tests, X-ray photographs, etc.) are already, as a standard, filled in, based on the selected guideline-form. The doctor can always deviate from this proposed standard.
6—The doctor decides additional tests: blood and X-ray photography, and completes the request form on the screen.
7—After having received the results on the same day or later the doctor states his opinion in a dialogue-screen.
8—The next procedure or guideline step is selected on the basis of this opinion.
9—At the next consultation the guideline determines the content of the consultation form. This brings the process back to item 5.

Finally, what is essential, is whether the implementation of a guideline step or deviation from a guideline step leads to the intended effect. For this reason the method of the invention constitutes the basis for effectivity and efficiency measurements on the basis of which guidelines can be corrected and new guidelines can be developed. This can be a task for a coordinating center and/or a scientific association.

By virtue of this evaluation property the method of the invention therefore constitutes a so-called "Quality System".

The association of the method according to the invention, as a tool, with the effect measurement it allows, gives indeed a very powerful quality system, which—taking into consideration the freedom for deciding and acting of the individual user:
- can offer insight in the effects of evaluation techniques and actions taken (in medical situations of the recovery or improvement in function of the analyses and therapies);
- can offer insight in the efficiency (such as costs) of evaluation techniques and actions taken;
- can form the basis for correcting the evaluation techniques and actions to be taken.

The invention claimed is:

1. Method for electronically storing, retrieving and/or modifying records using a computer system comprising a display unit, an input unit, a memory unit and a processing unit, and involving at least one recorded catalogue of recommended actions, comprising:
   using the computer system to sequentially steer a process of interrelated actions from said at least one recorded catalogue of recommended actions,
   creating a hierarchy of actions from the at least one recorded catalogue of recommended actions comprising hierarchised sequences of alternative actions,
   wherein each action specifies at least one act to be performed,
   wherein each level of the hierarchy represents recommended and alternative actions for a step in a procedure,
   wherein the procedure comprises a plurality of sequential steps, and wherein the recorded catalogue of recommended actions represents at least one procedure;
   using the computer system to generate electronic evaluation forms hierarchically organized as forms and subforms, wherein said evaluation forms comprise a list of one or more selected from the group comprising of recommended actions, information-input requests, decision-requests and selection algorithms, and wherein said generation of evaluation forms is carried out in function of said hierarchised sequences of alternative actions, and in function of the past history of all alternative actions, including both the actual action chosen and all other actions not chosen by the user, and
   using the computer system to link the generated evaluation forms for each traversal of the hierarchy and transfer the generated evaluation forms in one operation into one file.

2. Method according to claim 1, wherein said at least one recorded catalogue of recommended actions comprises associated electronic selection algorithms in respect of the hierarchised sequences of alternative actions.

3. Method according to claim 2, wherein said selection algorithms are integrated in said electronic forms.

4. Method according to claim 1, wherein said evaluation form comprises information from the records relevant for any decision-request involved in said evaluation form.

5. Method according to claim 1, wherein a record of information entered and used is stored in said memory unit.

6. Method according to claim 1, wherein a record of the information and actions entered and used is stored in the memory unit for the purpose of measurement of one or more selected from the group comprising of effectivity, efficiency of effects, and results of the procedure.

7. Method according to claim 1, wherein the method involves a supervising organization for the purpose of quality control and quality improvement of the method.

8. Method according to claim 1, wherein the method allows for the updating of the recorded catalogue(s) of recommended actions.

9. Method according to claim 6, wherein said supervising organization evaluates one or more selected from the group comprising of effectivity, efficiency of effects, and results based on said records of information and actions used/entered, stored during use of the method, and up-dates the recorded catalogue(s) of recommended actions in function of said evaluation.

10. A computer-readable storage medium holding computer-executable instructions for using a procedure as a guideline, the medium holding instructions for:
   providing at least one procedure to be used as a guideline, the procedure including a plurality of sequential procedure steps, each procedure step comprising a non-empty set of alternative actions, wherein each action specifies an act to be performed;
   encoding a set of rules for how to determine a next recommended action, wherein the next recommended action is which of the set of alternative actions in the next procedure step to recommend;
   encoding a set of rules for how to generate evaluation forms for the next recommended action;
   applying the procedure as a guideline, the instructions comprising:
      initializing a record for each application of the procedure as a guideline, the record storing information about the application of the procedure as a guideline;
      determining the next recommended action using the information in the record and the set of rules for how to determine the next recommended action;

generating a non-empty set of evaluation forms for the next recommended action using the information in the record and the set of rules for how to generate evaluation forms, each evaluation form including at least one of a recommended action, an information-input request, or a decision request, wherein at least one evaluation form informs a user of the method of the next recommended action, wherein the information-input request asks for information relevant to implementing the next recommended action, wherein the decision request asks for information about acts performed;

storing information entered into the set of evaluation forms into the record; and repeating the determining, generating, and storing instructions until the last step of the procedure has been completed, wherein the record for each application of the procedure as a guideline includes information about the procedure applied, the actions recommended, the acts performed, the evaluation forms generated, and the information stored.

11. The medium of claim 10, the instructions for applying the procedure as a guideline further comprising instructions for:

adding at least one user-selected evaluation form to an application of a procedure step; and storing information entered into the user-selected evaluation form into the record.

12. The medium of claim 10, wherein the set of evaluation forms for each procedure step includes information from the record relevant to at least one of the information-input request or the decision request in the set of evaluation forms.

13. The medium of claim 10, wherein each procedure step is represented as a non-empty set of process forms, wherein each process form comprises a non-empty set of subforms to be used in corresponding evaluation forms, and wherein the set of rules for how to determine the next recommended action are integrated into the set of process forms.

14. The medium of claim 10, the medium further holding instructions for:

transferring the record of an application of the procedure as a guideline into a single file in one operation.

15. The medium of claim 10, the medium further holding instructions for:

evaluating at least one of effectiveness, efficiency, or results of the procedure by analyzing records of using the procedure as a guideline.

16. A system for using a procedure as a guideline, comprising:

at least one procedure to be used as a guideline, the procedure including a plurality of sequential procedure steps, each procedure step comprising a non-empty set of alternative actions, wherein each action specifies an act to be performed;

a set of rules for each procedure for how to determine a next recommended action, wherein the next recommended action is which of the set of alternative actions in the next procedure step to recommend;

a set of rules for each procedure for how to generate evaluation forms for the next recommended action;

a record for each application of the procedure as a guideline, the record storing information about the application of the procedure as a guideline;

a memory for storing the procedures, sets of rules, and records; and a processor for executing instructions for applying the procedure as a guideline, the instructions comprising instructions for:

initializing a record for each application of the procedure as a guideline, the record storing information about the application of the procedure as a guideline;

determining the next recommended action using the information in the record and the set of rules for how to determine the next recommended action;

generating a non-empty set of evaluation forms for the next recommended action using the information in the record and the set of rules for how to generate evaluation forms, each evaluation form including at least one of a recommended action, an information-input request, or a decision request, wherein at least one evaluation form informs a user of the method of the next recommended action, wherein the information-input request asks for information relevant to implementing the next recommended action, wherein the decision request asks for information about acts performed;

storing information entered into the set of evaluation forms into the record in memory; and repeating the determining, generating, and storing instructions until the last step of the procedure has been completed, wherein the record for each application of the procedure as a guideline includes information about the procedure applied, the actions recommended, the acts performed, the evaluation forms generated, and the information stored.

17. The system of claim 16, the instructions for applying the procedure as a guideline further comprising instructions for:

adding at least one user-selected evaluation form to an application of a procedure step; and storing information entered into the user-selected evaluation form into the record.

18. The system of claim 16, wherein the set of evaluation forms for each procedure step includes information from the record relevant to at least one of the information-input request or the decision request in the set of evaluation forms.

19. The system of claim 16, wherein each procedure step is represented as a non-empty set of process forms, wherein each process form comprises a non-empty set of subforms to be used in corresponding evaluation forms, and wherein the set of rules for how to determine the next recommended action are integrated into the set of process forms.

20. The system of claim 16, the processor further executing instructions for:

transferring the record of an application of the procedure as a guideline into a single file in one operation.

21. The system of claim 16, the processor further executing instructions for:

evaluating at least one of effectiveness, efficiency, or results of the procedure by analyzing records of using the procedure as a guideline.

* * * * *